(12) United States Patent
Hwang et al.

(10) Patent No.: US 10,398,493 B2
(45) Date of Patent: Sep. 3, 2019

(54) HEATING SYSTEM

(71) Applicant: National Cheng Kung University, Tainan (TW)

(72) Inventors: Sheng-Jye Hwang, Tainan (TW); Huy-Tien Bui, Tainan (TW); Yu-Hsien Lin, Taichung (TW); Yi-San Chang, Tainan (TW); Huei-Huang Lee, Tainan (TW); Durn-Yuan Huang, Tainan (TW); Xi-Zhang Lin, Tainan (TW)

(73) Assignee: National Cheng Kung University, Tainan (TW)

( * ) Notice: Subject to any disclaimer, the term of this patent is extended or adjusted under 35 U.S.C. 154(b) by 170 days.

(21) Appl. No.: 15/539,687

(22) PCT Filed: Dec. 31, 2014

(86) PCT No.: PCT/CN2014/096038
§ 371 (c)(1),
(2) Date: Jun. 25, 2017

(87) PCT Pub. No.: WO2016/106736
PCT Pub. Date: Jul. 7, 2016

(65) Prior Publication Data
US 2017/0348039 A1 Dec. 7, 2017

(51) Int. Cl.
*A61B 18/12* (2006.01)
*A61B 18/04* (2006.01)
(Continued)

(52) U.S. Cl.
CPC ............. *A61B 18/12* (2013.01); *A61B 18/04* (2013.01); *A61B 18/08* (2013.01); *A61B 18/10* (2013.01);
(Continued)

(58) Field of Classification Search
CPC ......... A61B 18/08; A61B 18/09; A61B 18/10; A61N 1/40; A61N 1/403; A61N 2/00
See application file for complete search history.

(56) References Cited

U.S. PATENT DOCUMENTS

| | | | | |
|---|---|---|---|---|
| 8,540,705 B2* | 9/2013 | Mehta | ................... | A61B 18/14 606/31 |
| 9,039,698 B2* | 5/2015 | Ormsby | ............ | A61B 18/1815 606/41 |
| 2011/0077451 A1* | 3/2011 | Marchitto | .............. | A61B 18/14 600/13 |

FOREIGN PATENT DOCUMENTS

| | | |
|---|---|---|
| CN | 2090257 U | * 12/1991 |
| CN | 2090257 U | 12/1991 |

(Continued)

OTHER PUBLICATIONS https://www.edaboard.com/showthread.php?246796-Enamelled-wire-question-what-does-UEW-mean (Year: 2012).*

(Continued)

*Primary Examiner* — Linda C Dvorak
*Assistant Examiner* — Raghav C. Atluri (57) ABSTRACT

A heating system includes a power supply module, a regulatory module, electrically connected to the power supply module, for modulating the power supply module, and a heating module. The heating module includes a positioning device and a conductive device. The heating module is electrically connected to the power supply module and the regulatory module, and the conductive device is tightly wound around the positioning device.

7 Claims, 9 Drawing Sheets

(51) Int. Cl.
*A61B 18/08* (2006.01)
*A61B 18/10* (2006.01)
*A61F 7/12* (2006.01)
*A61N 2/00* (2006.01)
*A61B 17/00* (2006.01)
*A61B 18/00* (2006.01)

(52) U.S. Cl.
CPC ...... *A61F 7/12* (2013.01); *A61B 2017/00084* (2013.01); *A61B 2018/00089* (2013.01); *A61B 2018/00577* (2013.01); *A61B 2018/00595* (2013.01); *A61B 2018/00702* (2013.01); *A61B 2018/00791* (2013.01); *A61N 2/00* (2013.01)

(56) References Cited

FOREIGN PATENT DOCUMENTS

| CN | 201414837 Y | * | 3/2010 |
| CN | 201414837 Y |   | 3/2010 |

OTHER PUBLICATIONS https://www.techpowerup.com/articles/overclocking/134 (Year: 2006).*
https://www.fastenal.com/en/75/magnetisnn-in-stainless-steel-fasteners (Year: 2009).*
International Search Report of PCT Patent Application No. PCT/CN2014/096038 dated Sep. 23, 2015.

\* cited by examiner

HEATING SYSTEM

FIELD OF THE INVENTION

The present application relates to a heating system, especially related to a heating system using inner induction heating and resistance heating principles.

BACKGROUND OF THE INVENTION

"Heat" is a very important immune response activate factor for organisms. Due to tissues and cells' low heat-resisting capabilities, thermal therapy has been used for removal of harmful tissues and cells.

Thermal therapy primarily uses heat to burn tissues and cells, tissues and cells subjected to high temperature can be damaged and deteriorated, and hence easily removed.

Radio Frequency Ablation (RFA) and Microwave Ablation (MWA) are the two most widely used thermal therapy technologies; however these two therapies are markedly costly and cause the burdens on patients. In view of this, thermal therapy instruments which apply sorts of heating theories start to emerge and evolve. For instance, thermal therapy instruments which apply external induction heating are very common now. External induction heating uses a high energy external induction heater to generate an extracorporeal alternating magnetic field to heat up the magnetic material put in the organism or the percutaneous needle made of magnetic put in the tissue and thus achieves therapeutic purposes. Nevertheless, external induction technology gives rise to many problems, such as: magnetic force fails to penetrate deep enough in the body, needle production and material selection are both difficult, and clinical operations might raise safety concerns due to the high magnetic field strength.

In addition to external induction heating, thermal therapy instruments which applied the principle of resistance heating also existed. Traditional resistance thermal therapy embedded resistance as thermal conductivity substrate in the cautery needle, and achieved therapeutic effect by electrothermic reaction which produced heat at the point of the needle; however the diameter of the cautery needle were often too large because the thermal conductivity substrate required a certain size.

Since commonly used thermal therapy systems still need many more improvements, the applicant of the present application, after developed this application with careful research, makes the use of the thermal therapy more widely available and easier to operate in order to reduce health care costs.

SUMMARY OF THE INVENTION

In one aspect, the present application provides a heating system, having a power supply module; a regulatory module, electrically connected to the power supply module, for modulating the power supply module, and a heating module, having a positioning device and a conductive device. The heating module is electrically connected to the power supply module and the regulatory module, and the conductive device tightly winds around the positioning device. When the heating system functions, the conductive device will be heated up because of the resistance heating effect.

In one embodiment, the heating module further has a functional device, disposed in the vicinity of the conductive device, and the functional device will be heated up while the heating system functions because of electromagnetic induction action.

In one embodiment, the functional device surrounds the conductive device.

In one embodiment, the positioning device is a thermocouple device, the conductive device is an enameled wire, the functional device is a magnetic induction device, and a thermal paste is applied between the enameled wire and the magnetic induction device.

In one embodiment, the enameled wire is a UEW and NY (nylon covered by polyurethane) wire with a diameter of 0.08-2.00 mm, the magnetic induction device is SUS 304 or SUS 316 stainless steel, and the electric current of the power supply module is 0.1-5 A while the voltage is between 1.5-40 V.

In one embodiment, the regulatory module is a frequency-regulate module and/or temperature-regulate module.

In one embodiment, the regulatory module is a proportional-integral-derivative controller module.

In another aspect, the present application provides a heating system having a power supply module, and a heating module having a conductive device and a magnetic induction device. The conductive device is electrically connected to the power supply module, and while the heating system functions, the magnetic induction device is heated up because of electromagnetic induction action, and the conductive device is heated up because of resistance heating effect.

In one embodiment, the conductive device has a conductive coil and a positioning device, and the conductive coil is tightly wound around the positioning device.

In one embodiment, the magnetic induction device is wound around the conductive coil; the conductive coil is a UEW and NY (nylon covered by polyurethane) enameled wire with a diameter of 0.08-2.00 mm; the magnetic induction device is SUS 304 or SUS 316 stainless steel, and the electric current of the power supply module is 0.1-5 A while the voltage is between 1.5-40 V.

Broadly speaking, the present application provides a heating system having a heating module, a power supply system and a monitoring system. It combines the principles of inner induction and the resistance heating to build a heating system, winding the conductive coil tightly around the thermocouple and forming an induction coil, and then a percutaneous needle is put on. While applying, a high-frequency current passes through the conductive coil so the conductive coil generates an alternating magnetic field and induces the inner wall of the percutaneous needle with low permeability materials to heat up, and is coupled with the conductive coil itself to form a resistance heating device based on the resistance heating effect. With these two heating principles, the thermal energy can be produced to achieve the purpose of heating.

Among these, it further has a resonant frequency which is closer and/or equal to the conductive coil to ensure a better rate of heating by adjusting the output of the power supply system frequency.

Through the followings figures and embodiments, the technical features, purposes and effect of the present application are more readily understandable for person having ordinary skill in the art.

BRIEF DESCRIPTION

The present application is further illustrated by the figures in conjunction with the embodiments below, in the following figures.

Wherein the figures are marked as follows:
AC Power supply
Cr Capacitance
Lr Equivalent inductance
1 Heating system
11 Power supply module
111 Oscillator chip
112 TLP250 photocoupler
113 IR 2111 circuit device
114 TC4421 chip
115 TC4421 chip
116 IGBT driver switch
117 IGBT driver switch
118 ACS712 Current measurement chip
12 Temperature monitoring and self-adjusting frequency module
121 Microprocessor (Arduino) (MCU) chip development board
122 TA7257P motor driver chip
123 Max6675 thermocouple chip
124 K-type thermocouple
13 Heating module
131 Heating coil
132 Outer needle
133 Thermocouple
134 Inner sheath
135 Needle
136 Tenon
137 Outer sheath
138 Thermal paste
2 Half-bridge series resonant converter
21 Oscillator IC
22 Switch driver IC
23 Rectifier
24 Filter
25 Half-bridge resonant converter
31 Microprocessor (Arduino)
41 Microprocessor (Arduino)
42 Oscillator IC
43 Driver switch IC
44 ACS 712 current measurement IC

DETAILED DESCRIPTION

By the followings embodiments, the technical features, purposes and effect of the present application can be understandable and hence be enabled to practice for person having ordinary skill in the art. However the practices of the present invention shall not be limited by the following embodiments to those types of practices.

Figure 1:
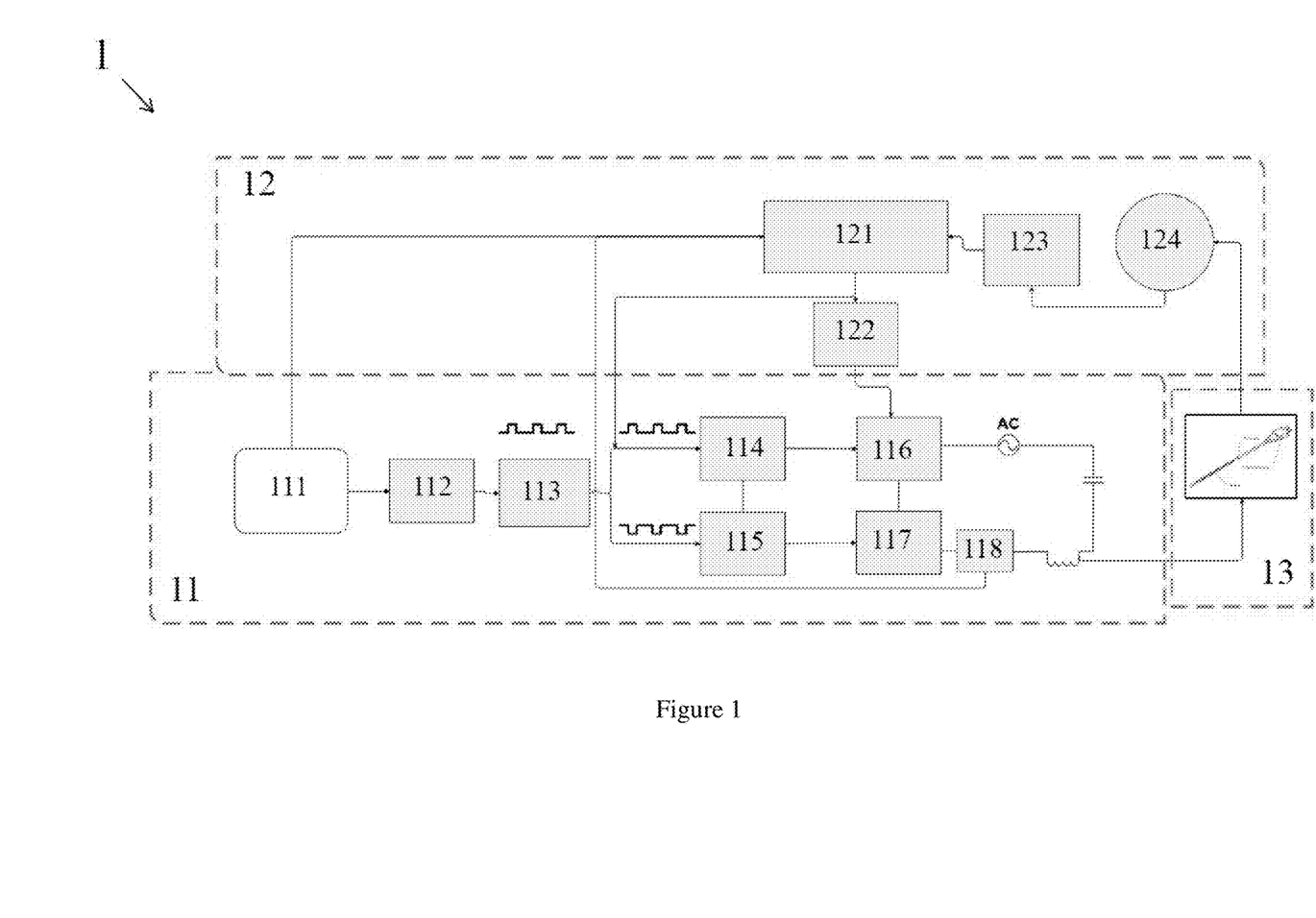
FIG. 1 is an illustration presenting the heating system of an embodiment in the present application.

Please see FIG. 1, which is an illustration presenting the heating system of an embodiment in the present application. As shown in FIG. 1, in this embodiment the heating system 1 has a power supply module 11, a temperature monitoring and self-adjusting frequency module 12 and a heating module 13. The power supply module 11, the temperature monitoring and self-adjusting frequency module 12, and the heating module 13 are electrically connected to each other. In this embodiment, the heating module 13 is a cautery needle module, the power supply module 11 further has an Oscillator 11, a TLP250 photocoupler 112, an IR 2111 circuit device 113, a TC4421 chip 114, a TC4421 chip 115, an IGBT driver switch 116, an IGBT driver switch 117 and an ACS712 current measurement chip 118. The temperature monitoring and self-adjusting frequency module 12 further has a microprocessor (Arduino) (MCU) chip development board 121, a TA7257P motor driver chip 122, a Max6675 thermocouple chip 123 and a K-type thermocouple 124.

In one embodiment of the present application, the power supply module 11 is developed on the induction heating principle and is able to adjust the energy output of the supply voltage from 3 to 40 V and the frequency from 20 to 100 kHz, and a converter applied (not shown) switches the DC power to high frequency AC power and provides to the load as a heating energy source.

Figure 2:
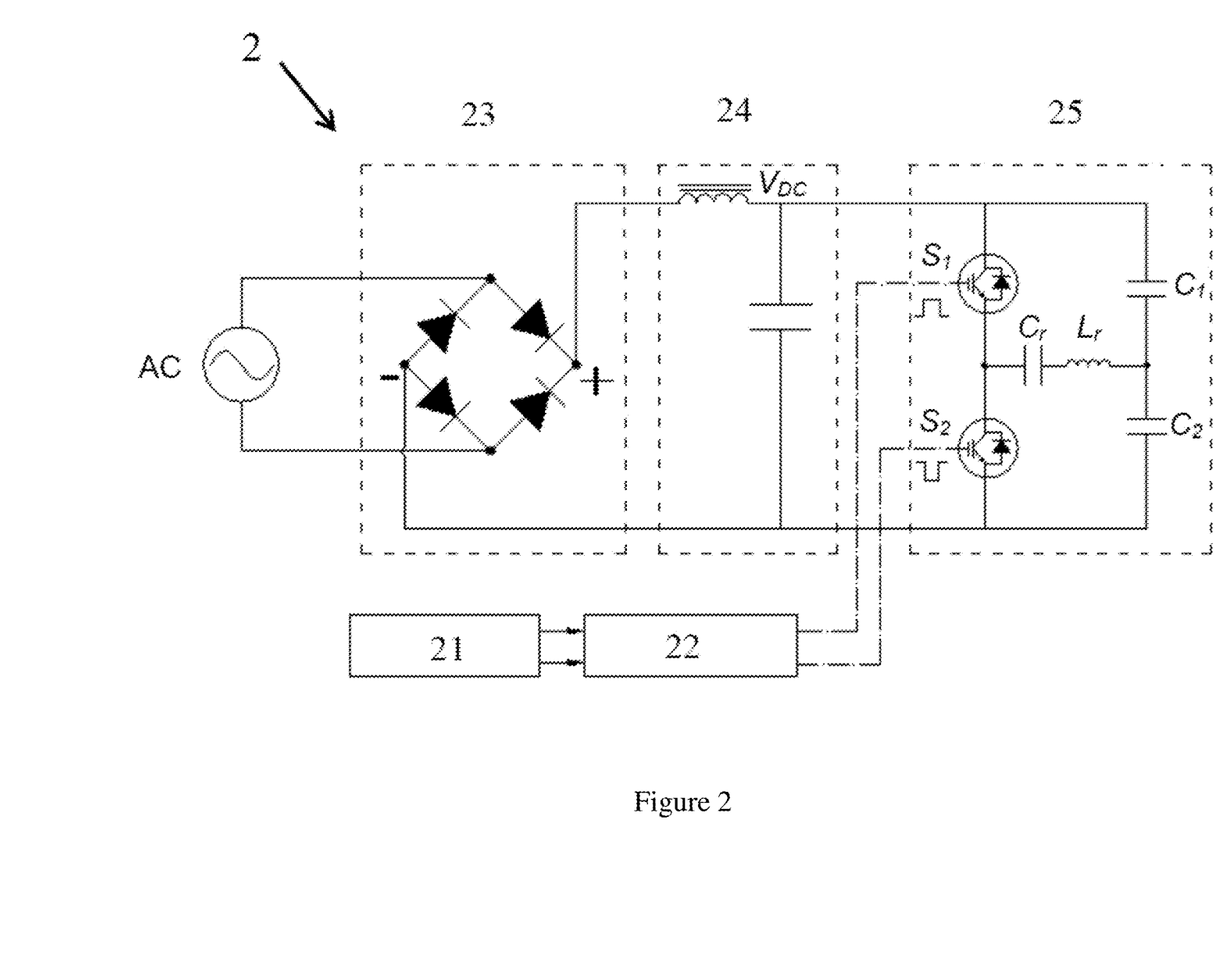
FIG. 2 is an illustration presenting a power supply made up of half-bridge series resonant converter of an embodiment in the present application.

In one embodiment, the needed power supply module is made up by a half-bridge series resonant converter (as shown in FIG. 2). In the embodiment of FIG. 2, while the half-bridge series resonant converter 2 switching frequency is higher than the resonant frequency, the power switch has zero voltage switching condition, and when the half-bridge series resonant converter 2 switching frequency is lower than the resonant frequency, the power switch has zero current switching condition. When circuit operation is under light load condition, the current of the resonant tank is relatively small, and the loss of the switch is smaller, thus the efficiency can be improved. In this embodiment, the half-bridge series resonant converter 2 includes:

Power AC: Household single phase AC voltage 110V;
Rectifier 23 and Filter 24: providing rectification and filtering functions, and generating a stable DC voltage;
VDC, using a commercially available power supply S-40-12 Mean Well, its specifications are 12V for output voltage and 3.5 A for output current;
Half-bridge resonant converter 25: in this embodiment, an IGBT model GT60M303 is selected to be its driver switch, having 50% switch duty cycle respectively, this design has the advantages of high efficiency and fast switching speed, which is suitable for high frequency operation;
Oscillator IC 21: the frequency signal generating unit, in this embodiment, an oscillator along with a microprocessor (the Arduino) provides a range of frequencies to facilitate frequency changing; MC74HC74AN, AD654JN, 2904D and IRF 7805, etc., are applied to compose an oscillator;
Switch driver IC 22: the driver switch unit, a TLP250 photocoupler is applied to establish an isolation circuit and to facilitate the transfer of driver control signal in different voltage level. Circuit device IR2111 is applied to receive the frequency signal transmitted by the Oscillator unit, then the signal is amplified and transmitted to TC4421, amplifying the voltage for the two IGBT driver switches and further generate high frequency AC power distributed to the load to activate;

Equivalent inductance Lr; and
Capacitance Cr.

Figure 3:
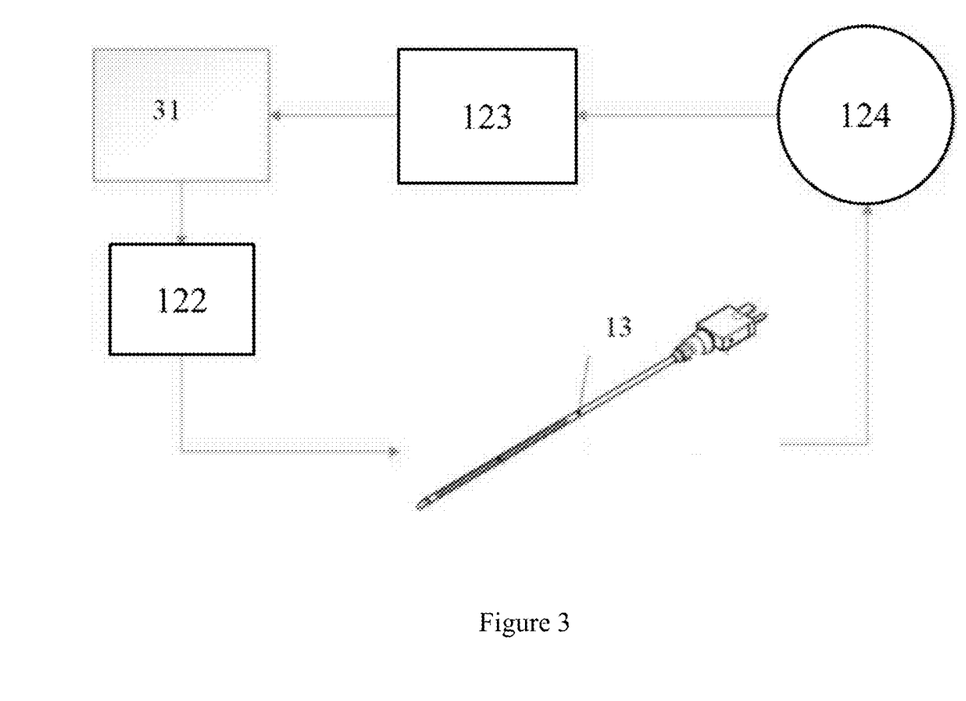
FIG. 3 is an illustration showing the operational principle of a temperature monitoring module of an embodiment in the present application.

FIG. 3 is an illustration presenting the operational principle of a temperature monitoring module of an embodiment in the present application. As shown in FIG. 3, the temperature control module in this embodiment, the K-type thermocouple 124 and the heating module 13 collocate with each other, and a microcontroller (Arduino) 31 is applied, the model of Mega 2560 single-chip development board designing proportional-integral-derivative controller (PID controller) is used to control temperature, and it works with Visual Studio software so that the User Interface written can input the maximum temperature needed and monitor real-time state of temperature rising. With respect to temperature monitoring, the peripheral circuit uses MAX6675 thermocouple chip 123 and TA7257P motor driver chip 122. There are two main functions in the MAX6675 thermocouple chip 123: turning the analog temperature signals into digital signals for the microprocessor (Arduino) single-chip to read; and having a gain effect which amplifies the signal so that the read millivolts (mV) can be readable by the chip gain value to be further transferred and calculated. TA7257P Motor driver chip 122 is applied, by a microprocessor (Arduino) 31 PWM pin (output voltage 0~5V) and by a proportional-integral-derivative controller (PID controller) theory, to adjust the output voltage and achieve the temperature monitoring, whereby the temperature feedback control is conducted. Proportional-integral-derivative controller (PID controller) has been widely used on a variety of control systems because of its high reliability and stability, and is a common feedback loop component in industrial control system.

This embodiment is based on Ziegler-Nichols method to adjust the Proportional-integral-derivative controller (PID controller), by using suitable Proportional-integral-derivative controller (PID controller) parameter, so that the temperature can have a faster increase rate, the temperature rising curve can meet the need, to achieve the temperature designate at the end and be steadily deduced by time.

The temperature control of the proportional-integral-derivative controller (PID controller) in the embodiment is set by the error value of the actual temperature and the set temperature. Before the operation, based on several isolated pork liver experiments, the coil length and the reference value of voltage have been decided, as shown in Table 1, wherein, in one embodiment, the heating coil applies a UEW and NY (nylon covered by polyurethane) enameled wire with a diameter 0.08 mm, however it should be adjusted according to the real situation. For instance, if it's used in an in vivo experiment, a higher voltage is needed than which is used in an isolated pork liver experiment, or if the temperatures of isolated pork livers vary, they will all have influences, too.

TABLE 1

Coil lengths and voltages disposal table

| Coil lengths (cm) | 1 | 1.5 | 2 | 3 | 4 | 5 |
|---|---|---|---|---|---|---|
| Voltage (V) | 15 | 16 | 18 | 20 | 22 | 22 |

In induction heating design, the working frequency is a very important factor to consider, it is strongly related to the performance of the heating system. The greater current flows through the induction coil, the greater the magnetic flux it produces, therefore it is possible to increase the eddy current generated in the workpiece by increasing the electric current in the induction coil, and thereby to enhance the heating effect so that the workpiece is heated up faster. In addition, eddy current intensity is also related to the cross-sectional size of the metal, the shape of the cross-section, the conductivity and the depth of penetration. When the output frequency matches, most part of the eddy current masses densely in induction coil at the front end, and the site away from the induction coil will not be heated up comparatively, but there is still a little bit of energy mainly transferred from the heated site due to thermal conduction. However it's not enough to excessively raise the temperature. Because the electric current in the induction coil has the critical influence to the heating effect, when the output frequency is close to or equal to the resonant frequency, the circuit can be regarded as a pure resistive circuit, under this circumstance most part of the energy which the power supply provides is transferred to the resistance, the electric current consequently reaches its maximum value, the adjusted induction coil frequency should be as close as possible to the resonant frequency.

Figure 4:
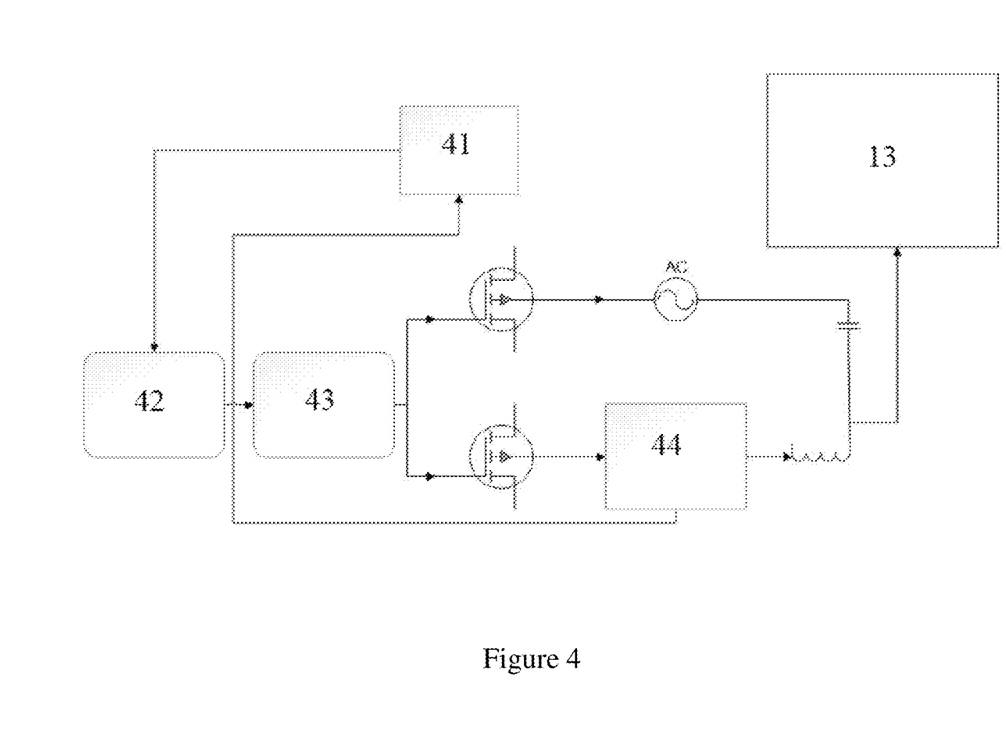
FIG. 4 is an illustration showing the operational principle of self-adjusting frequency of an embodiment in the present application.

FIG. 4 is an illustration presenting the operational principle of self-adjusting frequency of an embodiment in the present application. As shown in the FIG. 4, in the embodiment, a microprocessor (Arduino) 41 is applied to transfer PWM signal (0~5V) to the oscillator IC 42, and two adjustable resistances are applied to respectively set 0.1 V as the minimum value and 5V as the maximum value of scanning frequency. Then the oscillator IC 42 adjusts the frequency signal proportionally based on the voltage value received and transfers it to the Driver switch IC 43, and to drive IGBT to output high frequency AC power to the load. At this moment, the electric current value input to the load is measured by the ACS 712 Current measurement IC 44 and transferred to the microprocessor (Arduino) 41, then the electric current received at the time while the PWM voltage value is output is recorded, and a cycle is completed. After that the output frequency is adjusted by altering the various PWM signal value, and the current is measured and recorded. Following the cycle the scanning of the frequency between 20 to 100 kHz is completed, the a program is written to compare the values of these current recorded to choose a frequency with the highest current value to input to the load, and to complete a frequency self-adjustment, hence the induction heating efficiency of the heating module 13 can be or close to be optimized.

From the induction heating theory it's known that, when the electric current achieve its maximum in an induction coil, the input frequency is close to and/or equal to the resonant frequency. In addition, the induction coil can influence the inductance value by its number of turns, length and density, and that can affect the characteristic of intensity of the measured electric current, and thus in this embodiment, the frequency with the maximum current is searched by scanning the current changes in the frequency range.

Figure 5:
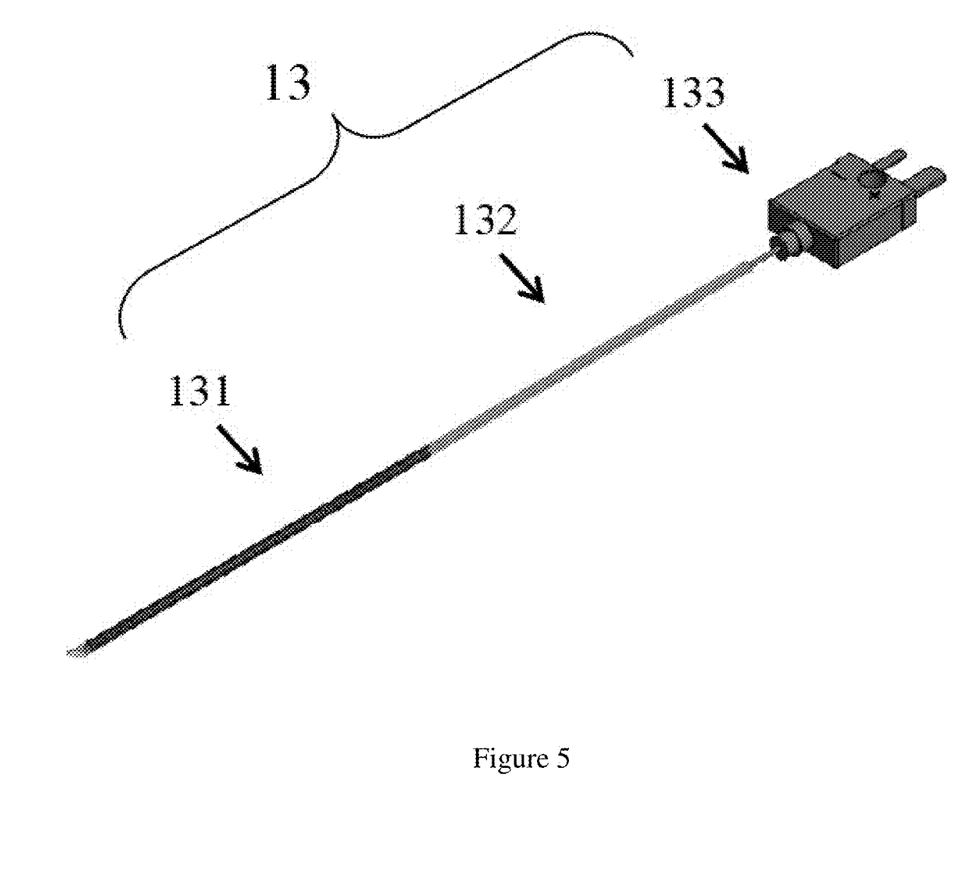
FIG. 5 is an illustration showing the heating module of an embodiment in the present application.

Please see FIG. 5, which is an illustration presenting the heating module of an embodiment in the present application. As shown in FIG. 5, in this embodiment, the heating module 13 is a cautery needle module, having: the thermocouple 133, the outer needle 132 and the heating coil 131. In this module, the front end of the thermocouple 133 is wound around by the heating coil 131 in the single-core winding method and forms a concentrated-heating-coil sector, and then it's placed inside the outer needle 132 to establish a cautery needle module. In one embodiment, the heating coil 131 is an enameled wire with a diameter of 0.08 mm and having the value of thermal resistance temperature of 200° C. In one embodiment, a PTC puncture needle in medical use which is specialized for viscera puncture is selected to be the outer needle 132. In addition, since the PTC puncture needle is mainly made of stainless steel materials SUS 304 or SUS 316, which can have low permeability materials after a series of processes like heating, perforation, drawing, etc., it's consistent with the needs for outer tube needle of the present application. In one embodiment, the applied 18-gauge PTC puncture needle has the outside diameter of 1.24 mm, inside diameter of 0.96 mm and the length of 150 mm. It should be noted that, for the purpose of cauterization, the hollow part at the front-end of the PTC puncture needle should be sealed to avoid causing problems such as blood or tissues leak into the needle. In one embodiment, the thermocouple 133 applies K-type thermocouple temperature probe, which uses stainless steel materials SUS 314 or SUS 316 to coat the internal metal wire part, with a certain rigidity for coils to be tightly wound on. The specification of the heating coil includes 0.5 mm diameter, 200 mm length and heat-resisting 800° C. temperature. In one embodiment, the heating coil 131 applies a UEW and NY ((nylon covered by polyurethane) enameled wire with a diameter 0.08 mm. This kind of enameled wire has excellent winding performance under high speed or automatic winding, providing coils and windings with high production densities, and has good quality factors, excellent adhesion and flexibility under high frequency, its advantages also include the ability to avoid damage when winding and so on, and its thermal endurance temperature is 200° C. When the current input is rather small, the enameled wire's voltage endurance can be 30-40 V, hence in this specification, the power supply specification is about 30 W, the current applied is not greater than 1.5 A, the voltage is not greater than 40 V. In other embodiments, the enameled wire is a UEW and NY ((nylon covered by polyurethane) enameled wire with diameter of 0.08-2.00 mm, and its magnetic induction device is SUS 304 or SUS 316 stainless steel, the electric current of the power supply module is 0.1-5 A while the voltage is between 1.5 to 40V. Moreover, if the frequency matches, only the site of the heating coil would be heated up significantly.

Figure 6:
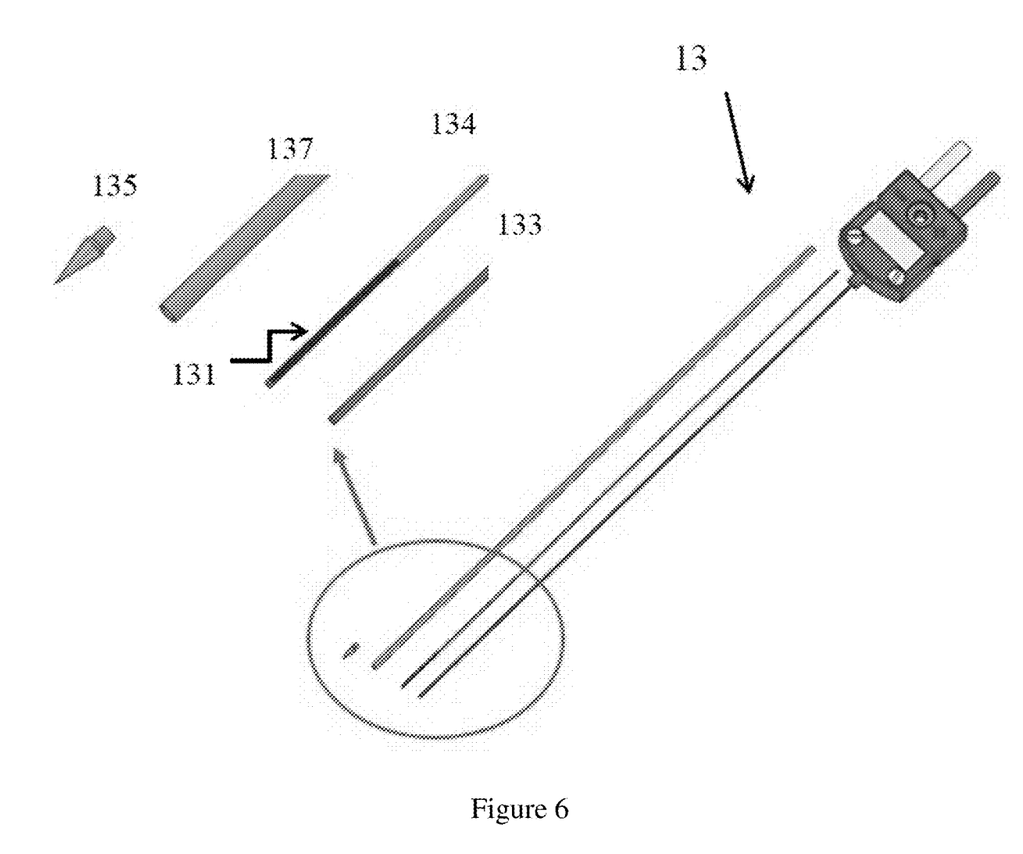
FIG. 6 is an illustration showing the heating module of an embodiment in the present application.
Figure 7:
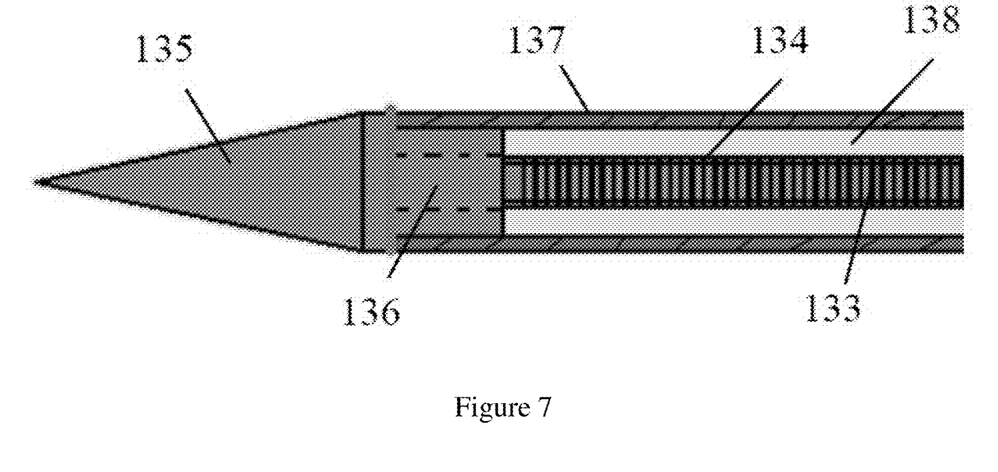
FIG. 7 is an illustration presenting a cross section of the heating module of an embodiment in the present application.

FIG. 6 is an illustration presenting the heating module of an embodiment in the present application. As shown in FIG. 6, the heating module 13 has the thermocouple 133, the inner sheath 134, the heating coil 131, the outer sheath 137 and the needle 135. The thermocouple 133 is inside the inner sheath 134, the heating coil 131 is wound tightly outside the inner sheath 134, and the thermocouple 133, the inner sheath 134, and the heating coil 131 are clad in the outer sheath 137. The inner sheath 134 is made of SUS 304 stainless steel material, with outside diameter of 0.69 mm and inside diameter 0.55 mm. The relative disposition between the inner sheath 134 (length: 210 mm) and the thermocouple 133 (length: 200 mm) is applied to have the temperature detecting point appear in the biggest central region of the heating coil 131 to help measure the most precise temperature. In one embodiment, the thermocouple 133 is disposed in the inner sheath 134, and the outer sheath 137 is made of SUS 304 stainless steel material and combined with the needle 135, the needled 135 is made into a cone shape to facilitate processing and penetrating, there is a resembling tenon 136 which is mainly for the function of position leading and fixing when placing the inner sheath 134. The outer sheath 137 and the needled 135 are combined together precisely by laser welding. As shown in FIG. 7, in one embodiment, the efficiency of heat conduction between the outer sheath 137 and the inner sheath 134 can be enhanced by applying the thermal paste 138.

In one embodiment of the present application, a power supply system (with proportional-integral-derivative controller (PID controller)) and a set of a heating module can collocate to control multiple power supply systems by a microprocessor (Arduino). In this way, it prevents the problem of excessive temperature difference due to the issue of voltage and current distribution which is caused by the situation that a single power supply system provides multiple needles; and it facilitates that if there is a need for more heating modules, simply adding new power supply system can then add the number of needles to the amount wanted and hence avoid issue of voltage and current distribution and causing other problems.

In Vivo Animal Experiment

In one embodiment, the outside and inside diameters of the 18-gauge PTC puncture needle applied are respectively 1.24 mm and 0.96 mm, the length is 150 mm; the K-type thermocouple temperature probe applies stainless steel SUS 314 or SUS 316 material to cover its internal metallic wire and has certain rigidity to allow the coils winding on it, the specifications of thermocouple temperature probe are 0.5 mm for diameter, 200 mm for length, 800° C. for thermal endurance temperature. In one embodiment, the heating coil 133 applies a UEW and NY (nylon covered by polyurethane) enameled wire with a diameter 0.08 mm. Moreover, if the frequency matches, only the site of the heating coil at the front end of the PTC needle would be heated up, and the site away from the heating coil will not be heated up comparatively.

Swine selected from Xinhua Livestock Research Institute of National Cheng Kung University are operated in surgical operation in cooperation with medical staff from the Institute. The experimentation mainly uses two kinds of coil lengths (1.5 and 3 cm) and is divided into two experiments, the 1.5 cm needles (two) are inserted into swine from the outside in coordination with the ultrasound imaging device, and the 3 cm needle are inserted into the liver directly after the operation to observe the volume and shape of liver ablation.

Percutaneous Puncture Experimental Condition:
The temperature set: 120 or 110° C.
The length of the coil: 1.5 cm
Heating time: 5, 10 min
Voltage output: 18V
Frequency: 34 kHz (matched frequency)

Firstly, cut open the abdomen of the swine and directly insert the needle into to liver, and the experimental condition is as follows
The temperature set: 120° C.
The length of the coil: 3 cm
Heating time: 10 min
Voltage output: 22V
Frequency: 30 kHz (matched frequency)

Figure 8A:
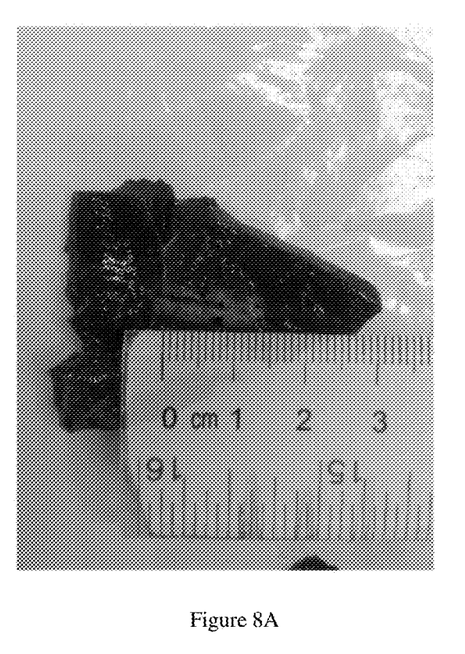
FIGS. 8A and 8B show the result of a puncture test with applying 1.5 cm heating coil.
Figure 8B:
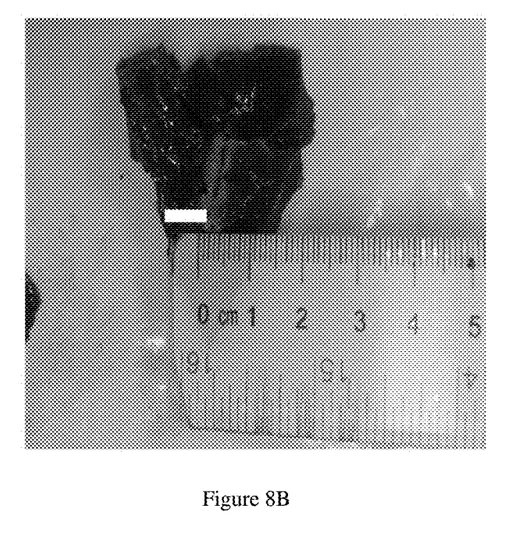
Figure 9:
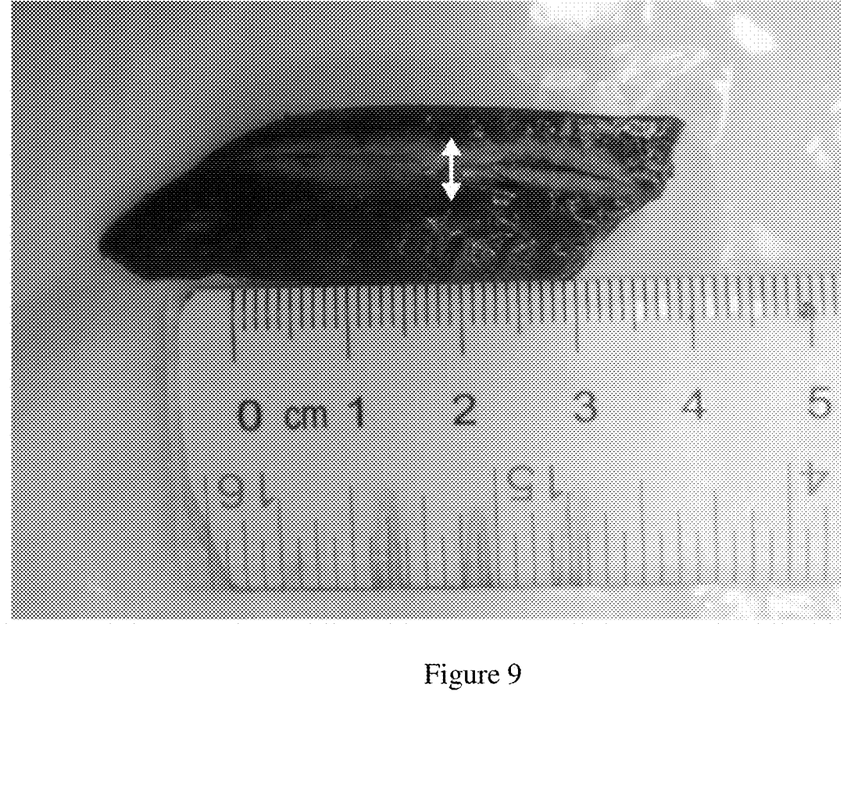
FIG. 9 is the result of a puncture test which applies 3 cm heating coil.

FIGS. 8A and 8B show the results of a puncture test applying 1.5 cm heating coil; FIG. 9 is the result of a puncture test applying 3 cm heating coil. As the experimental results shown by FIGS. 8A and 8B and FIG. 9, the needle structure developed in the present application has enough strength to percutaneous puncture swine's skin, and is able to rise to the temperature for hemostasis shortly in about 30 seconds. Additionally, with suitable output voltage in the liver of the swine in vivo it can effectively rise to the set temperature with apparent ablation area.

In the foregoing embodiment, the present application proposes a heating system, which integrates and develops components including heating module, power supply system and monitoring system, and it has been proved that this application is highly feasible by practices. In the embodiment, it combines inner induction heating and resistance heating these two principles to design the heating modules, the wire tightly winds around the thermocouple to form an induction coil, the outer sheath are clad in a puncture needle with low permeability. Then by making a high-frequency current pass through the conductive coil to generate an alternating magnetic field, the inner wall of the puncture needle with low permeability is induced to heat up, with the section of the conductive coil itself forms a resistance heating device due to resistance heating principle, the purpose of heating to specific region is achieved because of the thermal energies generated by two principles. In addition, with the temperature and frequency control, the needed temperature is set and the temperature rising condition is monitored with the assistance of the human machine interface of a computer. In one embodiment, if the most suitable power supply frequency of a heating module is known, the temperature and frequency regulatory module can be omitted by directly operating the power supply module. In another application, if the heating properties of the heating coil and the sheath it tightly winds around are known, the thermocouple can be replaced by other positioning devices. Furthermore, although the verification of the present application is an in vivo animal experiment, the scope of usages of the present application is not limited to medical applications, as long as the usage involves electric resistance heating and inner induction heating together at one time, it shall not been seen out of the desired scope of protection in the present application.

From the foregoing description of embodiments and results of the experiment, it has been adequately interpreted that the present application has successfully developed a heating system by the way of combining inner induction and resistance heating, and the present application is significantly different from the heating systems which use inner induction or resistance heating system alone. It is possible to achieve expected effects by controlling various conditions by microprocessor (Arduino) program. Generally, the embodiments of the present application have possessed the following specific achievements:

1. Successfully development and verification the heating effects of inner induction and resistance heating combination
2. The developed needles can be smaller or equal to 18-gauge.
3. The developed needles for thermal therapies are able to use SUS 304 or SUS 316 stainless steel, which are the same as the materials used in current medical system.
4. The developed system has been proved able to heat up the in vivo tissues.
5. Self-adjusting frequency module technique is part of adaptive control, and it can be applied to high frequency induction heating or energy storage and charging system.
6. Successfully development of multiple needles ablation and it is possible to enlarge the ablation cross-section area.

The foregoing description combines figures to describe the embodiments of the present application, but the present application is not limited to the above specific embodiment, the above embodiments are only demonstrative but not restrictive, by the revelation of the present application, without departing from the spirit of the present application and the claimed scope of protection, the person having ordinary skill in the art can accomplish many forms, which are all parts of the protection in the present application.

The invention claimed is:

1. A heating system, characterized in that, the heating system comprises:
    a power supply module;
    a regulatory module, electrically connected to the power supply module, for modulating the power supply module; and
    a heating module, comprising a positioning device, a conductive device and a functional device; wherein the heating module is electrically connected to the power supply module and the regulatory module, the conductive device is tightly wound around the positioning device to form an induction coil for generating, an alternating magnetic field, and the functional device is disposed in the vicinity of the conductive device; wherein the conductive device is an enameled wire, the functional device is a magnetic induction device, the enameled wire is a UEW and NY wire with a diameter of 0.08-2.00 mm, the magnetic induction device is SUS 304 or SUS 316 stainless steel, and the electric current of the power supply module is 0.1-5 A while the voltage is between 1.5-40 V.

2. The heating system as claimed in claim 1, characterized in that the functional device surrounds the conductive device.

3. The heating system as claimed in claim 2, characterized in that the positioning device is a thermocouple device, and a thermal paste is applied between the enameled wire and the magnetic induction device.

4. The heating system as claimed in claim 1, characterized in that the regulatory module is a frequency-regulate module and/or temperature-regulate module.

5. The heating system as claimed in claim 1, characterized in that the regulatory module is a proportional-integral-derivative controller module.

6. A heating system, characterized in that the heating system comprises:
    a power supply module, and
    a heating module comprising a conductive device and a magnetic induction device; wherein the conductive device is electrically connected to the power supply module; wherein the conductive device comprises a conductive coil, the conductive coil is a UEW and NY enameled wire with a diameter of 0.08-2.00 mm, the magnetic induction device is SUS 304 or SUS 316 stainless steel, and the electric current of the power supply module is 0.1-5 A while the voltage is between 1.5-40 V.

7. The heating system as claimed in claim 6, characterized in that the conductive device comprises a positioning device, and the conductive coil is tightly wound around the positioning device to form an induction coil for generating an alternating magnetic field.

* * * * *